United States Patent [19]

Van Steenburg

[11] Patent Number: 4,698,837
[45] Date of Patent: Oct. 6, 1987

[54] ARMBOARD MOUNTING ASSEMBLY

[75] Inventor: Kip Van Steenburg, Sudbury, Mass.

[73] Assignee: Amatech Corporation, Concord, Mass.

[21] Appl. No.: 710,050

[22] Filed: Mar. 11, 1985

[51] Int. Cl.⁴ .............................................. H05G 1/00
[52] U.S. Cl. .................................... 378/208; 269/328
[58] Field of Search ............... 378/177, 180, 208, 209; 269/328; 128/134, 77

[56] References Cited

U.S. PATENT DOCUMENTS

| | | | |
|---|---|---|---|
| 2,588,124 | 3/1952 | Kizaur | 378/177 |
| 2,972,505 | 2/1961 | Weickgenannt | 269/328 |
| 3,540,719 | 11/1970 | Romney et al. | 269/328 X |
| 3,897,345 | 7/1975 | Foster | 378/208 |
| 3,947,686 | 3/1976 | Cooper et al. | 378/209 |
| 4,045,678 | 8/1977 | Rickard | 269/328 X |
| 4,145,612 | 3/1979 | Cooper | 378/208 |
| 4,146,793 | 3/1979 | Bergstrom et al. | 378/208 X |
| 4,181,297 | 1/1980 | Nichols | 378/208 X |
| 4,484,571 | 11/1984 | Velazquez | 269/328 X |
| 4,488,715 | 12/1984 | Comeau | 269/328 |
| 4,562,588 | 12/1985 | Ruf | 378/208 |

FOREIGN PATENT DOCUMENTS

| | | | |
|---|---|---|---|
| 2946987 | 6/1981 | Fed. Rep. of Germany | 269/328 |
| 2103932 | 3/1983 | United Kingdom | 269/328 |

Primary Examiner—Frederick R. Schmidt
Assistant Examiner—Steven P. Schad
Attorney, Agent, or Firm—Joseph S. Iandiorio; Douglas E. Denninger

[57] ABSTRACT

An armboard mounting assembly including an armboard having a proximate and a distal end, an armboard mount, and a joint for pivotably interconnecting the armboard and the armboard mount for enabling rotation of the armboard about a pivot axis. The rotatable armboard and armboard mount have at least one pair of adjacent sections, and the assembly further includes friction members (or alternate grippers) for providing gripping between said adjacent sections, said friction members being responsive to a downward force on the armboard between the pivot axis and the distal end for increasing gripping between the adjacent sections and inhibiting relative rotation about the pivot axis. Depending on the materials used, the armboard mounting assembly is radiologically translucent, NMR (nuclear magnetic resonance)-compatible, or both.

35 Claims, 8 Drawing Figures

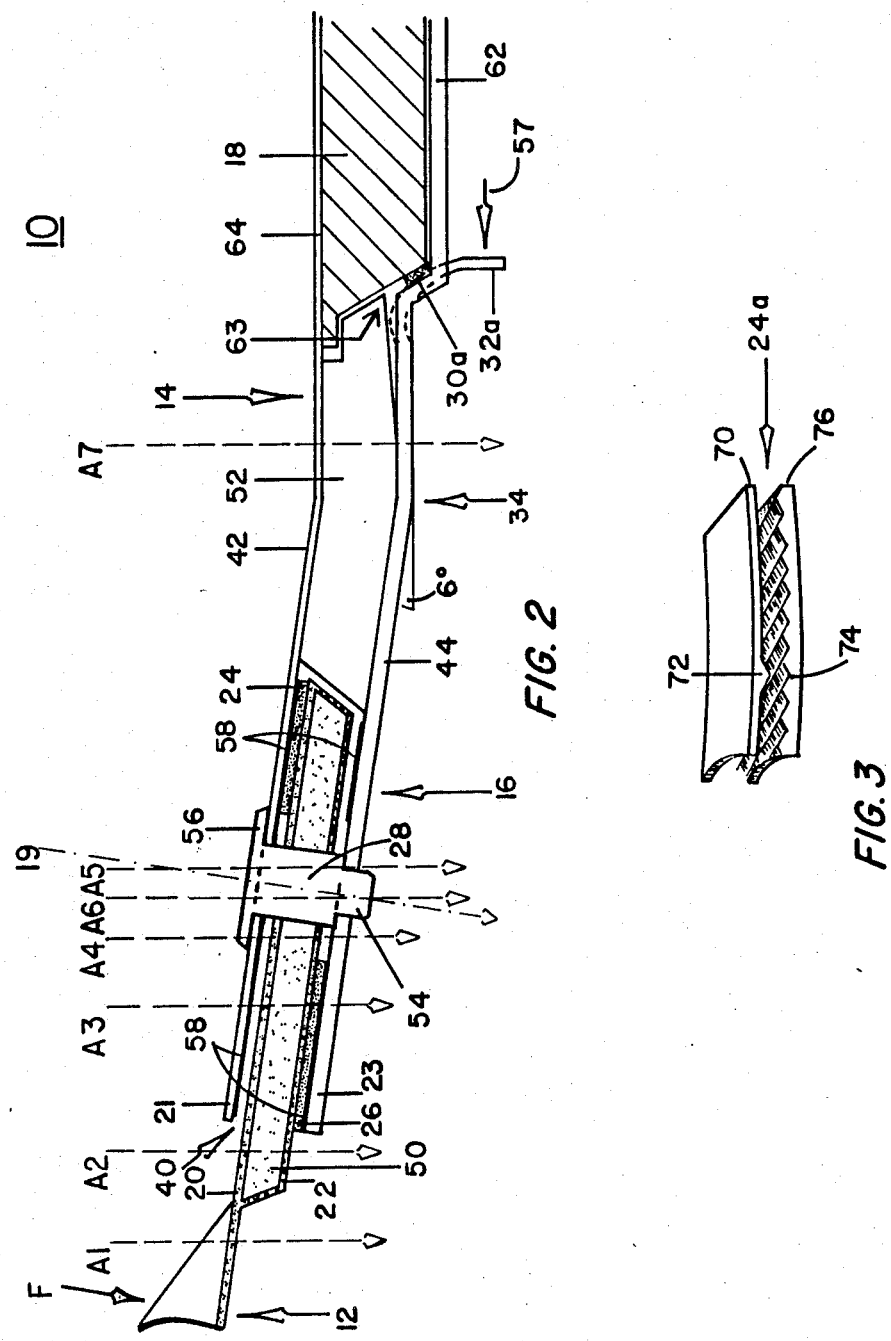

ARMBOARD MOUNTING ASSEMBLY

FIELD OF INVENTION

This invention relates to an armboard mounting assembly for imaging use and, more particularly, to an armboard mounting assembly which throughout is radiologically translucent, NMR-compatible, or both.

BACKGROUND OF INVENTION

Cardiac, neurological and general vascular studies frequently require an X-ray table for examining patients. Viewing a patient's body is particularly important for guiding catheters through arteries or veins. The body is frequently accessed through an arm of the patient positioned on an armboard of an armboard mounting assembly. This technique is commonly referred to as the Sones approach. An armboard mounting assembly has an armboard mount attached to the X-ray table for mounting one or more armboards which extend from the mounting assembly at a pivot assembly.

An X-ray table typically rests between a radiological source, such as an X-ray tube, and an imaging plate responsive to a viewing screen or including an imaging film. Most areas of conventional tables and armboards are by necessity radiologically translucent to allow X-rays to reach the imaging plate. However, important areas of X-ray tables and accessories often contain radiologically opaque structural material such as steel. Details of the patient's body overlying the opaque structure are obscured and physicians must navigate a catheter blindly through these bodily regions. One such region is the patient's shoulder overlying the pivot assembly between the armboard and the armboard mount. A conventional armboard has a steel pin protruding from a steel disk embedded in the board. Steel is used to provide strength and durability. Radiological opacity of the conventional pivot assembly presents great difficulty in passing a catheter through the proper vein or artery in the shoulder area. Further, the pivot assembly is often attached to the armboard mount with steel connector pins. Commonly, the connector pins insert into a steel cradle mount which bridges the X-ray table and provides support for opposing armboards. These radiologically opaque structures further reduce the effective viewing areas of a patient.

Conventional armboards exhibit other disadvantages. Accepted hospital practices prevent radiologists from touching objects outside the sterile zone. The locking mechanism for many armboards are located on the underside of the armboard and table in a non-sterile area, where it may not be accessed during medical procedures. Thus the need to move the armboard and the restriction against touching non-sterile areas can create a conflict for the attending physicians. These locks are active locking systems requiring action to lock or unlock them. When locked, it is possible to damage them through forcible, inadvertant movement. Armboard mounts are secured with separate active locking systems often involving screws or clamps which are not X-ray translucent.

The armboards themselves are often uncomfortable for the patient. The board typically rotates in a plane parallel to the surface of the table underneath the outer part of the patient's shoulder, or even the upper arm. But the human arm inclines naturally from the scapular area and the arm is more comfortable when rotated on a slight incline originating in this region. Further, present armboards are not equipped with radiologically translucent extensions adjustable to accommodate arms of varying length. Nor are they adjustable to permit the width of the armboard to be offset to one side of a patient's arm to provide greater working surface for the physicians. Physicians often place tubes, instruments or other equipment along one side of a patient's arm. It is desirable for this equipment to travel with the arm as the latter is repositioned during the course of the examination. Simply widening the armboard presents handling difficulties, particularly when the S.I.D. (Source Image Distance) must be minimized. Such S.I.D. constraints are involved when the imaging stand is rotated about the longitudinal axis of the imaging table for lateral viewing.

The metal components associated with conventional armboard designs make them incompatible with NMR procedures. NMR scanning requires that the study area be free of ferrous or other magnetic material which is or can become magnetized. The magnetic material interferes with the varying magnetic field used in NMR procedures. The study area must also be free of electrically conductive material for the safety of the patient and the attendants. These requirements have prevented the use of a pivoting, locking armboard during such procedures.

SUMMARY OF INVENTION

It is therefore an object of this invention to provide an improved armboard mounting assembly for radiological studies.

It is a further object of this invention to provide an improved armboard mounting assembly which is compatible with nuclear magnetic resonance (NMR) studies.

It is a further object of this invention to provide an improved armboard mounting assembly having a pivot assembly which is radiologically translucent.

It is a further object of this invention to provide such a pivot assembly having a more uniform attenuation profile.

It is a further object of this invention to provide such a pivot assembly providing smoother, easier rotation of the armboard.

It is a further object of this invention to provide such a pivot assembly which is NMR-compatible.

It is a further object of this invention to provide an improved armboard mounting assembly having an improved armboard locking system.

It is a further object of this invention to provide such a locking system which is passive and self-locking.

It is a further object of this invention to provide such a locking system which is locked by the weight of a patient's arm.

It is a further object of this invention to provide such a locking system which reduces the possibility of damage to the armboard from forcible movement.

It is a further object of this invention to provide such a locking system which is simply constructed and easy to repair and maintain.

It is a further object of this invention to provide such a locking system for use in NMR procedures that is free of all magnetic and electrically conductive materials.

It is a further object of this invention to provide such a locking system which provides easy operation without violating the sterile zone.

It is a further object of this invention to provide an improved armboard mounting assembly which is more anatomically compatible with the patient.

It is a further object of this invention to provide an improved armboard mounting assembly having an armboard mount that is radiologically transparent.

It is a further object of this invention to provide such a mount which is self-locking to the radiological imaging table.

It is a further object of this invention to provide such a mount having fewer and simpler components.

It is a further object of this invention to provide such a mount which resists breakage from forcible movement.

It is a further object of this invention to provide such a mount which is compatible with NMR studies.

It is a further object of this invention to provide an improved armboard mounting assembly having an armboard which is adjustable in length.

It is a further object of this invention to provide such an armboard which is adjustable in width.

The invention features an armboard mounting assembly which is radiologically translucent, NMR-compatible, or both. There is an armboard having a proximate end and a distal end, an armboard mount, and means for pivotably interconnecting the armboard and the armboard mount for enabling rotation of the armboard about a pivot axis. The rotatable armboard and armboard mount have at least one pair of adjacent sections. The invention further includes means for providing gripping between the adjacent sections, said means being responsive to a downward force on the armboard between the pivot axis and the distal end for providing gripping between the adjacent sections and inhibiting relative rotation about the pivot axis.

In one embodiment, the means for pivotably interconnecting includes a pivot pin, and the means for providing gripping includes engaging means. The engaging means may include a friction member mounted on at least one of the adjacent sections, or may include a detent on one adjacent section and a recess on the other for receiving the detent. The armboard mount may include a pair of spaced segments for receiving the proximate end of the armboard therebetween and the armboard and armboard mount define two pairs of adjacent sections. The means for providing gripping may then include engaging means mounted on at least one section of each pair of sections. The armboard and armboard mount are angled upwardly from a region of the armboard mount inward of the proximate end of the armboard; the region may be positionable to underlie the scapular area of a patient.

In the radiologically translucent embodiment, the armboard, armboard mount, means for pivotably interconnecting, and means for providing gripping are radiologically translucent. The armboard and armboard mount may be made of carbon fiber and the armboard mounting assembly may further include attenuating means disposed on at least one of the adjacent sections for balancing radiological attenuation, such as by compensating for attenuation produced by the means for providing gripping. The attenuating means may be mounted on the armboard mount.

In the NMR-compatible embodiment, the armboard, armboard mount, means for pivotably inteconnecting, and means for providing gripping consist of non-magnetic and electrically non-conductive materials. The armboard and armboard mount may be made of unidirectional fiberglass or Kevlar.

In a preferred embodiment, the armboard mount includes mount gripping means for engaging an object on which the armboard mount is to be installed, and a biasing member for releasably urging the mount gripping means against the object. The mount gripping means may be fixed to the biasing member and include a friction member. The biasing member may include a flexible element. The armboard mount includes a pair of spaced legs for receiving the object, such as an X-ray table, and the flexible element is attached to one of the legs and may be integral with one of the legs. The pivot pin may be made of ABS plastic or Micarta.

The mounting assembly may further include an armboard extension slidably mounted on the armboard by at least one pair of opposing flanges. Each flange overlaps a portion of an edge of the armboard between its proximate and distal end. The armboard extension may have a width greater than that of the armboard, and the armboard and armboard extension may have similar contours. The armboard extension may include means, such as velvet, disposed on at least one portion which is in contact with the armboard for minimizing abrasion to the surface of the armboard.

The invention further features a radiologically translucent and/or NMR-compatible armboard for rotatably mounting relative to an armboard mount. The armboard has a proximate end and a distal end, and means for pivotably interconnecting the armboard to the armboard mount for enabling rotation of the armboard about a pivot axis. The armboard further includes means for providing gripping between the adjacent sections to inhibit relative rotation of the armboard about the pivot axis, the means being responsive to a downward force on the armboard between the pivot axis and the distal end when mounted in the armboard mount.

The armboard and means for providing gripping may be radiologically translucent and the armboard may include attenuating means disposed on the armboard about the means for pivotably interconnecting and the means for providing gripping for providing increased radiological attenuation to compensate for the attenuation produced by the means for providing gripping. The armboard and means for providing gripping may consist of non-magnetic and electrically non-conductive materials. The means for providing gripping may include a friction member, the means for pivotably interconnecting may include a hole in said armboard for receiving a pivot pin, and an armboard extension may be slidably mounted on the armboard.

DISCLOSURE OF PREFERRED EMBODIMENTS

Other objects, features and advantages will occur from the following description of a preferred embodiment and the accompanying drawings, in which:

FIG. 2 is a cross-sectional view along lines 2—2 of FIG. 1;

FIG. 3 is an axonometric cross-sectional view of an alternative gripper for use in the device of FIG. 2;

Figure 1:
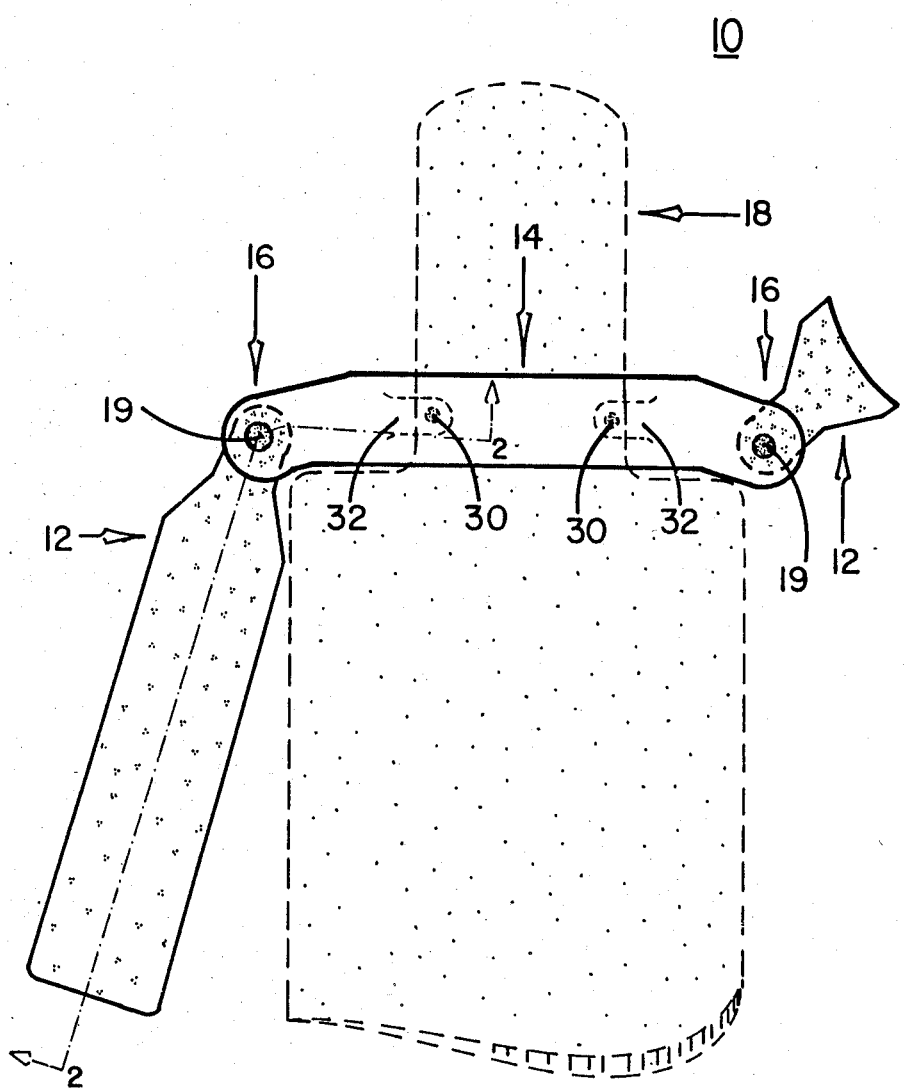
FIG. 1 is a plan view of an armboard mounting assembly according to this invention mounted on an X-ray table and including an armboard, an armboard mount, and a pivot assembly.

Armboard mounting assembly 10 is shown in FIG. 1 having armboards 12 and armboard mount 14 with integral pivot assemblies 16 which together rotatably support the arms of a patient lying on X-ray table 18, shown in phantom. Armboards 12 rotate about pivot axes 19. As described below, radiologically translucent components of an armboard mounting assembly according to this invention can be arranged to provide uniform radiological attenuation across a vertical profile of the armboard mounting assembly, facilitating examination of the patient. When the components are composed of non-magnetic and electrically non-conductive materials, the armboard mounting assembly can be used for NMR procedures.

Armboard mount 14 secures armboard mounting assembly 10 to an object such as X-ray table 18. Preferably, armboard mount 14 includes two mount gripping means 30, disposed on biasing members 32, for engaging X-ray table 18 on which armboard mount 14 is installed.

Armboard mount 14 is angled upwards, FIG. 2, at region 34 at an angle of 6° to provide a more comfortable position during rotation for a patient's arm located on armboard 12. Region 34 is located beneath the scapula of an average patient when lying on table 18. Armboard 12 rotates about pivot axis 19 through the center of pivot pin 28. The proximate end of armboard 12 includes circular insert 40 having edges slanted at approximately a 45° angle as discussed below. Insert 40 rests between two skins of armboard mount 14, designated spaced segments 42, 44. Section 20 of insert 40 is adjacent to section 21 of segment 42, and section 22 of insert 40 is adjacent to section 23 of segment 44. Grippers 24, 26 are mounted on the surface of sections 20, 22, respectively, and include a friction member composed of material such as natural gum rubber or Urethane Rubber, available from Parkway Rubber, Ohio. Alternatively, these high-friction brake members may be recessed into sections 20, 22. As described below, the area and thickness of these members affect radiological attenuation profiles. In yet another arrangement, the brake member may be one or more annular friction rings mounted about the circumference of a non-rotating pivot pin, the pivot pin being affixed to segment 42, 44, or both.

A downward force having a vector in the direction indicated by arrow F brings grippers 24, 26 against sections 21, 23 of spaced segments 42, 44, respectively, to increase gripping between these sections. The weight, however slight, of armboard 12 itself typically causes some engagement between grippers 24, 26 and sections 21, 23, respectively; alternatively, the initial engagement is negligible or nonexistent. Engagement is increased by additional downward force on armboard 12. The force such as that provided by the weight of a patient's arm is generally transverse to the direction of rotation and generally parallel to the pivot axis. Grippers 24, 26 oppose and restrict rotation but do not absolutely prevent rotation when normal downward force is applied to armboard 12.

Instead of friction members, the armboard mounting assembly may include a detent and recess arrangement to engage at least one pair of adjacent sections between armboard 12 and armtoard mount 14. Gripper 24a, FIG. 3, includes detent portion 70 which has projection 72 to engage one of the recesses 74 of recess portion 76. Gripper 24a may be located in the same region as gripper 24, FIG. 2, such that detent portion 70 and recess portion 76 are mounted on sections 20 and 21, respectively, of pivot assembly 16. It is desirable that either detent portion 70 or recess portion 76, or both, be arcuate such that armboard 12 may be moved through a large angle until its rotation is inhibited by application of downward force to the armboard. A rosette segment of 160°–180°, for example, may serve as recess portion 76.

To provide more uniform attenuation across a vertical section of pivot assembly 16, FIG. 2, radiologically translucent materials are preferred for armboard mounting assembly 10 when intended for radiological use. An acceptable material for radiological use of armboard 12 and armboard mount 14 is carbon fiber. Kevlar, available from Exxon Materials Division and Uniroyal, is also suitable, although somewhat thicker cross-sections are required to provide strength similar to carbon fiber. Insert 40 of armboard 12 may contain a core 50 and armboard mount 14 may contain core 52, the cores composed of ABS plastic material, without fire retardant additives, available from Uniroyal, or a phenolic material such as Micarta. Pivot pin 28 includes shouldered post 54 and head 56 and may also be formed from ABS plastic or Micarta. Pin 28 may be held in place simply by a piece of adhesive tape and may be formed without head 56.

A smooth durable braking surface is provided by wear-resistant materials such as Mylar 58, FIG. 2, disposed about the braking surfaces of sections 21 and 23 of segments 42 and 44, respectively. Mylar is particularly effective when the friction member is rubber since these two materials exhibit a high coefficient of friction when forced against each other. Mylar also provides slight radiological attenuation and is used to balance the attenuation caused by other elements in pivot 16. Depending on the attenuation characteristics of these other elements, Mylar or thin aluminum foil is disposed about at least one of the adjacent sections 20, 21, 22 and 23 to compensate for the attenuation provided by friction member grippers 24, 26 and to balance the attenuation of pivot pin 28.

Figure 4:
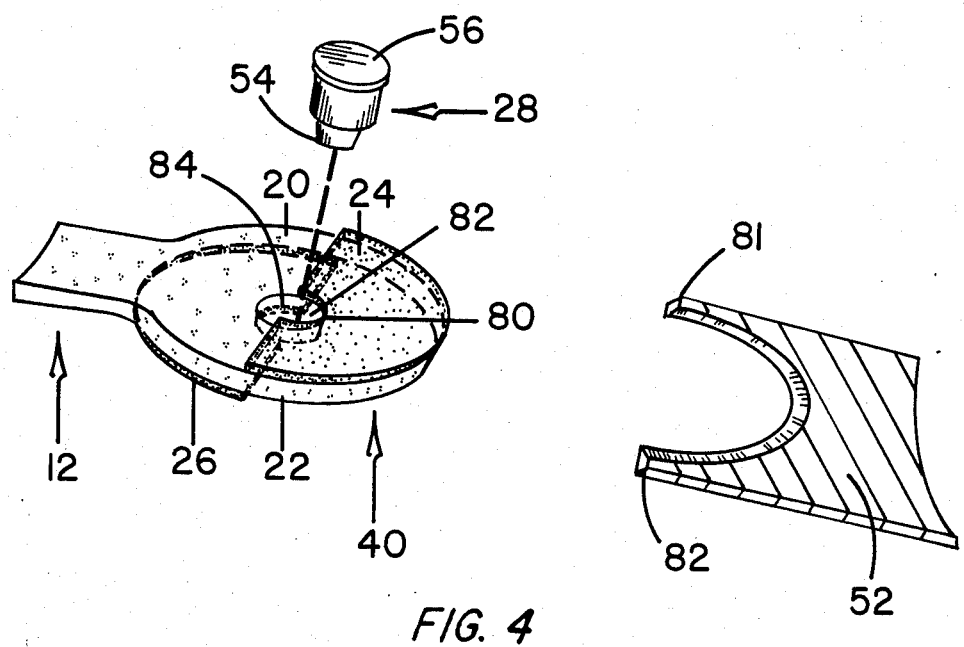
FIG. 4 is a partial axonometric view of a pivot assembly according to this invention.

Friction member grippers 24, 26 are semicircular in shape and mounted on sections 20, 22 as shown in FIG. 4. Grippers 24, 26 have openings 80 and 84, respectively, corresponding to the opening 82 in insert 40 for receiving pivot pin 28. The chamfered edge of post 54 projects through armboard mount segment 44 (not shown), while pin head 56 rests on the surface of segment 42 (not shown).

The end of core 52 that faces armboard insert 40 is semi-circular in shape to admit insert 40, FIG. 4. Core 52 projects outwardly on either side of insert 40 nearly as far as opening 82; the rotational boundaries of armboard 12 are determined by projections 82, 83. Core 52 is bonded to skin segments 42, 44 (not shown) to supplement tensile and compressive strengths of the two skins. Additional strength may be added by merging segment 44 with the edges of segment 42 to enclose the longitudinal sides of core 52.

The details of radiologically translucent components for one embodiment of the armboard mounting assembly, using the reference numerals of FIG. 2, are provided in Table I:

TABLE I
DETAILS OF ARMBOARD MOUNTING ASSEMBLY COMPONENTS

| REFERENCE NUMERAL | ELEMENT | MATERIAL | THICKNESS (inch) | ATTENUATION (in mm aluminum) |
|---|---|---|---|---|
| 24,26 | Friction Members | Urethane | .060 | .152 |
| 28 | Pivot Pin without Head and Post | A.B.S. | .655 | 1.529 |
| 12 | Armboard | carbon fiber | .060 | .255 |
| 50 | Armboard Insert Core | A.B.S. | .190 | .443 |
| 58 | Mylar | Mylar | .005 | .012 |
| 42 | Armboard Mount Segment, Top | carbon fiber | .060 | .255 |
| 44 | Armboard Mount Segment, Bottom | carbon fiber | .100 | .425 |
| 52 | Armboard Mount Core | A.B.S. | .375 | .874 |
| 56 | Pin Head only | A.B.S. | .070 | .163 |
| 54 | Pin Post only | A.B.S. | .180 | .419 |

The attenuation values in mm aluminum equivalents are approximations since attenuation does not vary linearly with thickness; the values are extrapolated from studies of similar thicknesses. For these components, vertical attenuation characteristics at viewing slice points indicated by dashed lines A1 through A7 are summarized in Table II:

TABLE II
VERTICAL ATTENUATION CHARACTERISTICS OF ARMBOARD MOUNTING ASSEMBLY

| SLICE | ELEMENT NO. COMBINATION | ATTENUATION (in mm aluminum) |
|---|---|---|
| A1 | 12 | 0.26 |
| A2 | 12 + 50 | 0.70 |
| A3 | 42 + 58 + 12 + 50 + 26 + 58 + 44 | 1.56 |
| A4 | 56 + 42 + 58 + 12 + 50 + 44 | 1.54 |
| A5 | (28 − 54) + 44 | 1.53 |
| A6 | 28 | 1.53 |
| A7 | 42 + 44 + 52 | 1.55 |

For example, radiological viewing slice A1 passes through only highly transparent armboard 12 having an attenuation of 0.26 mm of aluminum. Radiological slice A3 passes through armboard mount segments 42, 44, armboard 12, armboard insert core 50, friction pad 26, and two layers of Mylar 58 disposed on sections 21, 23. The components seen in view A3 provide an attenuation equivalent to 1.56 mm of aluminum.

Thus, a difference of only 0.03 mm aluminum-equivalent attenuation is provided in this example between viewing slices A3–A7, including the crucial pivot assembly components. While the slice attenuation values in Table II are based on approximations of the attenuation values for each element, the relative differences among the slice attenuation values are fairly accurate as presented. The slanted edges of armboard insert 40 and armboard mount core 52, FIGS. 2 and 4, further reduce transitions in the attenuation profile. The density, thickness, and shape of these elements are varied after fluoroscopic observation until a minimum level of contrasts is provided across the attenuation profile. The materials appropriate for NMR use are discussed below.

Reduced, more uniform radiological attenuation may also be provided for friction member 30a and biasing member 32a, FIG. 2, of armboard mount 14 which engage the X-ray table to secure armboard mounting assembly 10. Biasing member 32a releasably urges friction member 30a against table 18. Friction memter 30a is similar in composition to friction members 24, 26 and is attached to member 32a with epoxy. Spaced legs 62, 64, through which one portion of table 18 is received, may be lined with a protective material such as velvet to minimize abrasion tc the surface of table 18 and to aid slidable positioning of armboard mounting assembly 10. For convenience of manufacture, biasing member 32a is a flexible element which is an integral part of leg 62. Although the material at region 63 is shown at a slight distance from table 18 for clarity, leg 62 of armboard mount 14 may contact the table in this region.

Figure 5:
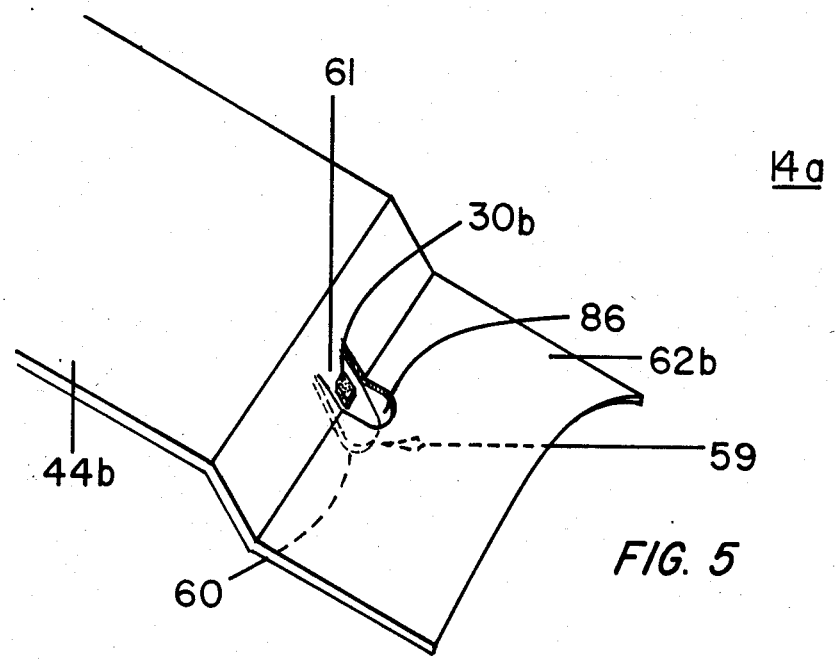
FIG. 5 is an axonometric view of a mount gripping means and biasing member according to this invention.

In one embodiment, the flexible element is formed of carbon fiber and is 0.100 inch in thickness, approximately ⅝ of an inch in width, and approximately 1½ inches long. The two edges and terminal end 60 of flexible element 59, FIG. 5, are cut out of the material of armboard mount 14a, including segment 44b and leg 62b, leaving end 61 attached and integral with the material. Friction member 30b is urged through opening 86 by flexible element 59 except when terminal end 60 of flexible element 59 is forced away from leg 62b by external pressure, bringing friction member 30b to the position shown in FIG. 5.

To adjust the position of armboard mounting assembly 10, outward pressure, arrow 57, FIG. 2, is applied to biasing member 32a near its terminal end to overcome its urging of friction member 30a against table 18. For example, a medical attendant may reposition armboard mounting assembly 10 by placing one thumb of each hand between flexible element 59 and table 18, applying force outwardly, arrow 57, from table 18 to both flexible elements 59 and moving armboard mount 14 toward or away from him.

Figure 6:
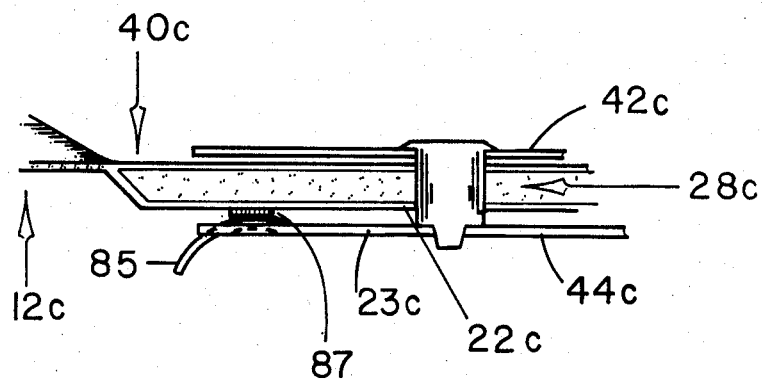
FIG. 6 is a partial cross-sectional view along lines 2—2 of FIG. 1 of an alternative pivot assembly.

A similar arrangement of one or more biasing members and friction members can be used as the locking mechanism in the pivot assembly. Member 85, FIG. 6, is located on section 23 of segment 44c and engages section 22c of armboard insert 40c. When biasing member 85 is a flexible element similar to flexible element 59, FIG. 5, its terminal end is also manually depressible to move the friction member away from adjoining section 22c of insert 40c to thereby allow rotation of armboard 12c about pivot pin 28c. Downward force on armboard 12c, although not necessary in this arrangement to inhibit rotation, will increase pressure and therefore friction between the friction member 87 and adjoining insert section 22c. Therefore, this arrangement is also responsive to downward force on armboard 12c to increase gripping between sections 22c and 23c.

When intended for NMR use, the armboard mounting assembly must not contain magnetic or electrically conductive materials. Urethane rubber, natural gum rubber, Mylar, A.B.S. plastic, and Kevlar are all compatible with NMR procedures. Another acceptable material is unidirectional, high-strength fiberglass. Unidirectional fiberglass or Kevlar may be used as the skins of armboard 12 and armboard mount 14 instead of carbon fiber. Since radiological attenuation is not considered in NMR procedures, the components are readily increased in thickness to provide increased structural strength.

Figure 7A:
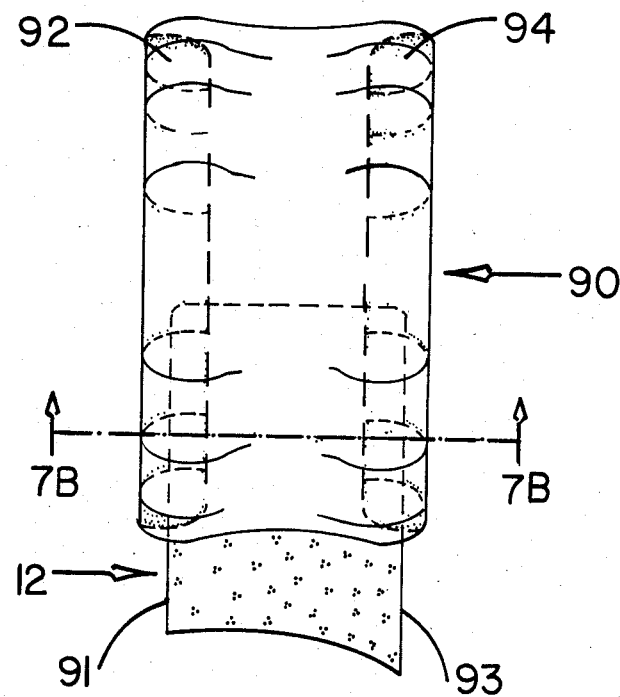
FIG. 7A is a schematic plan view of an armboard and armboard extension according to this invention.
Figure 7B:
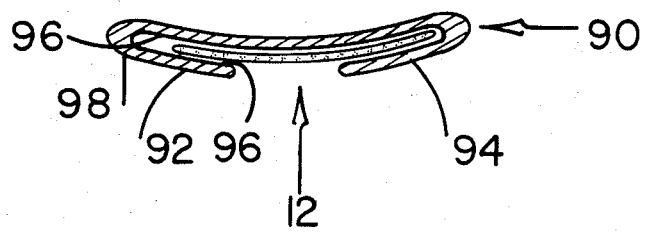
FIG. 7B is a cross-sectional view along lines 7B—7B of FIG. 7A.

To accommodate patients with longer arms, or to offset armboard width to provide a shelf which inherently follows the rotation of the armboard, armboard extension 90, FIG. 7A, is slidably mounted over armboard 12. As shown in cross-section, FIG. 7B, armboard extension 90 has at least one pair of flanges 92, 94 which overlap and partially underlie armboard 12. For convenience of manufacture, flanges 92, 94 are formed from and are integral with the armboard extension itself, as shown in FIG. 7A. Velvet or other cushioning or low-friction material may be added to portions of inner surface 96, FIG. 7B, to protect the surface of armboard 12 from abrasion and to aid slidability. Armboard 12 and armboard extension 90 have similar contours such that extension 90 nestles into armboard 12. For X-ray use, armboard extension 90 is preferably composed of radiologically translucent material such as carbon fiber, Kevlar or A.B.S. plastic to provide more uniform attenuation across the armboard mounting assembly. Kevlar, A.B.S. plastic, or fiberglass are suitable for NMR applications. Since structural support is provided by the armboard, the structural strength of the armboard extension is of diminished importance.

The width of armboard extension 90 may be substantially greater than that of armboard 12, as shown by offset portion 98. Armboard extension 90 may then be shifted laterally in relation to armboard 12 to provide additional working surface for attending physicians. This work surface can be offset to either side of armboard 12 according to space requirements. Where armboard 12, and therefore armboard extension 90, are angles upwardly from region 34, FIG. 2, of armboard mount 14, the armboard is positionable to overlie table 18, FIG. 1, when the projections of core 52 permit armboard rotation at an angle of at least 90° from the longitudinal axis of armboard mount 14. It is desirable for at least the inner edges of flanges 92, 94, FIG. 7A, to overlap a portion of each edge of 91, 93 of armboard 12 regardless of the lateral position of armboard extension 90 to properly secure the extension to the armboard.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An armboard mounting assembly comprising:
an armboard having a proximate end and a distal end;
an armboard mount;
means for pivotably interconnecting said armboard and said armboard mount for enabling rotation of said armboard about a pivot axis;
said rotatable armboard and armboard mount overlapping to define at least one pair of adjacent sections;
means for providing gripping between said adjacent sections to inhibit rotation about said pivot axis; said armboard, said armboard mount, said means for pivotably interconnecting, and said means for providing gripping being radiologically translucent; and
attenuating means, disposed on at least one of said adjacent sections, for balancing radiological attenuation among said adjacent sections, said means for pivotably interconnecting, and said means for providing gripping.

2. The armboard mounting assembly of claim 1 in which said means for pivotably interconnecting includes a pivot pin.

3. The armboard mounting assembly of claim 2 in which said pivot pin is made of A.B.S. plastic.

4. The armboard mounting assembly of claim 2 in which said pivot pin is made of Micarta.

5. The armboard mounting assembly of claim 1 in which said means for providing gripping includes engaging means.

6. The armboard mounting assembly of claim 5 in which said engaging means includes a friction member mounted on at least one of said adjacent sections.

7. The armboard mounting assembly of claim 6 in which said friction member is mounted on said armboard.

8. The armboard mounting assembly of claim 5 in which said engaging means includes a detent on one of said adjacent sections and at least one recess on the other for receiving said detent.

9. The armboard mounting assembly of claim 5 in which said armboard mount includes a pair of spaced segments for receiving the proximate end of said armboard therebetween.

10. The armboard mounting assembly of claim 9 in which said armboard and armboard mount define two pairs of adjacent sections and said means for providing gripping includes engaging means mounted on at least one section of each said pair of sections.

11. The armboard mounting assembly of claim 1 in which said armboard and said armboard mount are made of carbon fiber.

12. The armboard mounting assembly of claim 1 in which said attenuating means compensates for attenuation produced by said means for providing gripping.

13. The armboard mounting assembly of claim 1 in which said attenuating means is mounted on said armboard mount.

14. The armboard mounting assembly of claim 1 in which said armboard and said armboard mount are made of Kevlar.

15. The armboard mounting assembly of claim 1 in which said armboard, said armboard mount, said means for pivotably interconnecting, and said means for providing gripping consist of non-magnetic and electrically non-conductive materials.

16. The armboard mounting assembly of claim 15 in which said armboard and said armboard mount are made of undirectional fiberglass.

17. The armboard mounting assembly of claim 1 further including an armboard extension slidably mounted on said armboard by at least one pair of opposing flanges, each said flange overlapping a portion of an edge of said armboard between said proximate end and said distal end.

18. The armboard mounting assembly of claim 17 in which said armboard extension has a width greater than that of said armboard.

19. The armboard mounting assembly of claim 17 in which said armboard and said armboard extension have similar contours.

20. The armboard mounting assembly of claim 17 in which said armboard extension includes means, disposed on at least one portion of said armboard extension in contact with said armboard, for minimizing abrasion to the surface of said armboard.

21. The armboard mounting assembly of claim 20 in which said means for minimizing is velvet.

22. The armboard mounting assembly of claim 1 in which said attenuating means provides substantially uniform attenuation among said adjacent sections, said means for pivotably interconnecting, and said means for providing gripping.

23. The armboard mounting assembly of claim 1 in which said means for gripping is responsive to a downward force on said armboard between said pivot axis and said distal end to increase gripping between said adjacent sections and to inhibit relative rotation about said pivot axis.

24. An armboard mounting assembly comprising:
an armboard having a proximate end and a distal end;
an armboard mount;
said armboard and armboard mount being angled upwardly from a region of armboard mount inward of said proximate end of said armboard;
means for pivotably interconnecting said armboard and said armboard mount enabling rotation of said armboard about a pivot axis;
said rotatable armboard and armboard mount defining at least one pair of adjacent sections; and
means for providing gripping between said adjacent sections, said means being responsive to a downward force on said armboard between said pivot axis and said distal end for increasing gripping between said adjacent sections and inhibiting relative rotation about said pivot axis.

25. The armboard assembly of claim 24 in which said region is positionable to underlie the scapular area of a patient.

26. An armboard mounting assembly comprising:
an armboard having a proximate end and a distal end;
an armboard mount;
means for pivotably interconnecting said armboard and said armboard mount for enabling rotation of said armboard about a pivot axis;
said rotatable armboard and armboard mount defining at least one pair of adjacent sections;
means for providing gripping between said adjacent sections, said means being responsive to a downward force on said armboard between said pivot axis and said distal end for increasing gripping between said adjacent sections and inhibiting relative rotation about said pivot axis;
said armboard mount including mount gripping means for engaging an object on which said armboard mount is to be installed, and a biasing member for releasably urging said mount gripping means against the object, said biasing member including a flexible element; and
said armboard mount including a pair of spaced legs for receiving the object, and said flexible element being attached to one of said legs.

27. The armboard mounting assembly of claim 26 in which said mount gripping means is fixed to said biasing member.

28. The armboard mounting assembly of claim 26 in which said mount gripping means includes a friction member.

29. The armboard mounting assembly of claim 26 in which said flexible element is integral with one of said legs and is formed of the same material.

30. An armboard for rotatably mounting relative to an armboard mount comprising:
said armboard having a proximate end and a distal end;
said armboard having means for pivotably interconnecting said armboard to said armboard mount for enabling rotation of said armboard about a pivot axis;
means for providing gripping between said armboard mount and armboard to inhibit relative rotation of said armboard about said pivot axis, said means for providing gripping being responsive to a downward force on said armboard between said pivot axis and said distal end when mounted in the armboard mount; and
said armboard and said means for providing gripping being radiologically translucent and said armboard including attenutating means, disposed on said armboard about said means for pivotably interconnecting and said means for providing gripping, for balancing radiological attenuation among said adjacent sections, said means for providing gripping, and said means for pivotably interconnecting.

31. The armboard of claim 30 in which said armboard and said means for providing gripping consists of nonmagnetic and electrically non-conductive materials.

32. The armboard of claim 30 in which said means for providing gripping includes a friction member.

33. The armboard of claim 30 in which said means for pivotably interconnecting includes a hole in said armboard for receiving a pivot pin.

34. The armboard of claim 30 further including an armboard extension slidably mounted on said armboard by at least one pair of opposing flanges, each said flange overlapping a portion of an edge of said armboard between said proximate end and said distal end.

35. The armboard of claim 34 in which said armboard extension includes means, disposed on at least one portion of said armboard extension in contact with said armboard, for minimizing abrasion to a surface of said armboard.

* * * * *